(12) United States Patent
Querrey et al.

(10) Patent No.: US 11,287,406 B2
(45) Date of Patent: Mar. 29, 2022

(54) MULTI-INPUT AUTO-SWITCHING GAS SAMPLE CONDITIONING SYSTEM

(71) Applicant: Mustang Sampling, LLC, Ravenswood, WV (US)

(72) Inventors: Timothy L. Querrey, Ravenswood, WV (US); Nicholas S Wolfe, Ravenswood, WV (US)

(73) Assignee: Mustang Sampling, LLC, Ravenswood, WV (US)

( * ) Notice: Subject to any disclaimer, the term of this patent is extended or adjusted under 35 U.S.C. 154(b) by 186 days.

(21) Appl. No.: 16/847,191

(22) Filed: Apr. 13, 2020

(65) Prior Publication Data
US 2020/0326320 A1 Oct. 15, 2020

Related U.S. Application Data
(60) Provisional application No. 62/834,144, filed on Apr. 15, 2019.

(51) Int. Cl.
*G01N 33/00* (2006.01)
*G01N 1/40* (2006.01)
*G01N 1/44* (2006.01)

(52) U.S. Cl.
CPC ........... *G01N 33/0022* (2013.01); *G01N 1/40* (2013.01); *G01N 1/44* (2013.01); *G01N 33/0016* (2013.01)

(58) Field of Classification Search
CPC .. G01N 33/0022; G01N 33/0016; G01N 1/26; G01N 1/2247
See application file for complete search history.

(56) References Cited

U.S. PATENT DOCUMENTS

| 4,090,392 A * | 5/1978 | Smith ................. G01N 1/26 73/863.33 |
| 4,497,214 A * | 2/1985 | Ramelot .............. G01N 1/24 73/863.12 |
| 4,883,505 A * | 11/1989 | Lucero ................ G01N 1/34 73/864.81 |
| RE35,874 E | 8/1998 | Neeser et al. |
| 7,162,933 B2 | 1/2007 | Thompson et al. |
| 7,484,404 B2 | 2/2009 | Thompson et al. |
| 8,056,399 B2 | 11/2011 | Thompson et al. |
| 9,285,299 B2 | 3/2016 | Thompson |
| 9,562,833 B2 | 2/2017 | Thompson et al. |
| 10,215,739 B1 * | 2/2019 | St. Amant, III ... B01D 39/2027 |
| 2006/0000298 A1 * | 1/2006 | Thompson ........... G01N 1/2247 73/861.11 |

(Continued)

FOREIGN PATENT DOCUMENTS

WO 2015123302 A1 8/2015

OTHER PUBLICATIONS

European Search Report. dated Feb. 28, 2020.
U.S. PCT International Search Authority Search Report & Written Opinion for Application No. PCT/US20/28152, dated Jul. 2, 2020.

*Primary Examiner* — Francis C Gray
(74) *Attorney, Agent, or Firm* — Cahn & Samuels, LLP

(57) ABSTRACT

A gas sample and conditioning device for sampling gas in storage or transport device and conditioning the gas while automatically switching between input lines based on a characteristic of the gas sample. Multiple input lines are provided within allows for flow between different input lines based on the characteristic of the gas sample.

11 Claims, 1 Drawing Sheet

(56) References Cited

U.S. PATENT DOCUMENTS

| | | | |
|---|---|---|---|
| 2006/0234621 A1* | 10/2006 | Desrochers | G01N 1/26 |
| | | | 702/50 |
| 2010/0012201 A1 | 1/2010 | Welker et al. | |
| 2011/0016955 A1 | 1/2011 | Cormier | |
| 2016/0068777 A1 | 3/2016 | Menon et al. | |
| 2016/0238494 A1* | 8/2016 | Chrin, II | G01N 33/0073 |
| 2017/0167954 A1* | 6/2017 | Thompson | G01N 1/2247 |
| 2018/0209875 A1* | 7/2018 | Curtis | G05D 9/00 |
| 2018/0238797 A1* | 8/2018 | Sanroma | G01N 21/39 |

* cited by examiner

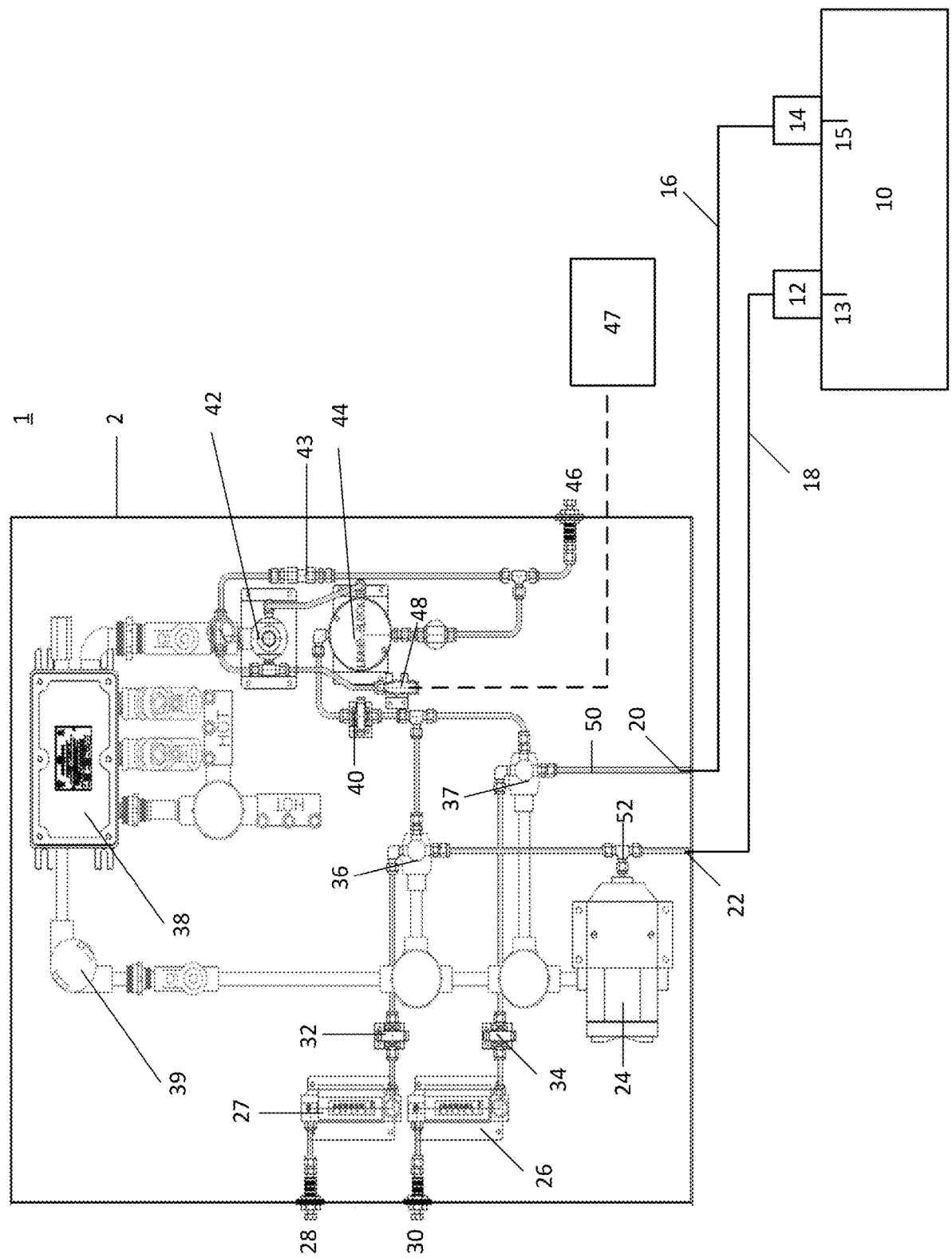

MULTI-INPUT AUTO-SWITCHING GAS SAMPLE CONDITIONING SYSTEM

FIELD OF THE INVENTION

This invention relates generally to systems and methods for collecting, analyzing, conditioning and maintaining samples of compositions in gaseous form. More particularly, the invention relates to providing multiple input auto-switched gas sample lines in the event of upstream interruptions in one or more of the gas sample lines or elsewhere in the system.

BACKGROUND OF THE INVENTION

Natural gas is a combustible gaseous mixture that can be essentially pure methane or composed of several different hydrocarbon compounds obtained from sources ranging from deep underground reservoirs formed by porous rock to renewable biogas sources. The composition of natural gas extracted from different reservoirs varies depending on the geographic location of the reservoir. In fact, it is not entirely uncommon for the composition of gas extracted from a single given reservoir to vary to an extent. Regardless of any variations, however, the primary component of natural gas is methane, a colorless, odorless, gaseous saturated hydrocarbon. Methane usually makes up from 80% to 95% of any natural gas sample and the balance is composed of varying amounts of ethane, propane, butane, pentane and other hydrocarbon compounds.

Natural gas is used extensively in residential, commercial and industrial applications. The utilization of Natural Gas for power generation is well known and growing in importance and popularity to substitute for classical fossil fuels such as oil and coal as a more ecologically benign alternative. It is the dominant energy used for home heating with well over half of American homes using natural gas. The use of natural gas is also rapidly increasing for electric power generation, cooling and as a transportation fuel.

Natural gas, like other forms of heat energy, is measured in British thermal units or Btu. One Btu is equivalent to the heat needed to raise the temperature of one pound of water by one-degree Fahrenheit at atmosphere pressure. A cubic foot of natural gas has about 1,027 Btu. Natural gas is normally sold from the wellhead, i.e., the point at which the gas is extracted from the earth, to purchasers in standard volume measurements of thousands of cubic feet (Mcf). However, consumer bills are usually measured in heat content or therms. One therm is a unit of heating equal to 100,000 Btu.

Accordingly, sampling and analysis of the natural gas along various points in the pipeline network has become an increasingly important endeavor. More particularly, because consumers are typically billed for natural gas in Btu's, it is important that the Btu measurement of any particular gas volume be accurate. Further, because various suppliers can, and do, supply gas, which comes from varying origins and geographic locations, to a common pipeline, the measured Btu value within a given section of pipe can vary.

Gas samples can be extracted via a probe from a gas pipeline. Once the gas sample is extracted, it can be provided through stainless steel tubing with a relatively small diameter to an analyzer, such a, a chromatograph, for analysis. A chromatograph is a device that utilizes a family of analytical chemistry techniques to separate mixtures into their constituent components. Typically, the techniques utilized by a chromatograph include separating the components of the mixture on the basis of differences in their affinity for a stationary and a mobile phase to identify an accurate composition of the gas. As gas chromatographs are extremely sensitive and expensive to fix, it is critical that the sampled gas be conditioned to the correct temperature and pressure to avoid partial or full phase change to a liquid phase before entering the gas chromatograph.

Problems can arise, however, when there is an interruption in the gas flow from the gas pipeline upstream of the system or when gas samples at inadequate pressures are passing through the steel tubing gas sample line. If there is inadequate pressure of the gas sample, a constituent gas sample which is not representative of the natural gas in the pipeline will be passed through the system for eventual analysis by the chromatograph. This can result in inaccurate analysis which in turn leads to inaccurate Btu readings. Further, if there is an interruption in flow, then the gas chromatograph will need to be quickly deactivated to avoid being damaged. Reactivation of a chromatograph is time-consuming and expensive.

According to one embodiment of the present invention, multiple gas sample input lines can be implemented from one or more pipeline take-off probes thereby providing multiple inputs of the gas sample to the system. This allows for one fully functioning gas sample input line to provide natural gas to the system in the event that there is a problem, such as pressure drops, upstream of the system in another sample input line. However, while this helps alleviate issues relating to inaccurate sampling or gas chromatograph shutdown due to inadequate pressure on the problematic gas sample input line, it can create issues with respect to making adjustments to deactivate one sample input line while activating another. These adjustments must be made manually and as the source of adjustment (i.e. valve) for each line are often spaced at a large distance (i.e. 100 feet), it greatly increases the labor and time required to update the settings of the lines. During this delay time prior to deactivating the problematic sample input line, gas samples which are not representative of the natural gas in the pipeline will be passed through the system leading to faulty analysis by the gas chromatograph and inaccurate Btu readings. Further, as control centers for monitoring gas flow and conditioning are often not near the pipeline sample points and/or valves themselves, it can be time consuming for a technician to locate and correct the pipeline flow. This results in lost production while system measurements are halted until the system can be manually adjusted to accept natural gas from an uninterrupted gas sample input line.

As for industrial applications, a typical facility that uses natural gas as a fuel source will conventionally provide a natural gas feed (pipeline or storage tanks) for communicating vaporized gas to a steam generator that powers electricity-generating turbines. For example, liquid natural gas (LNG) can be extracted from a storage tank, vaporized and passed through a feed line to a furnace for steam generation. Alternatively, the feedstock in a feedline can originate with a renewable biogas facility which must maintain an adequate pressure and flowrate for effective utilization. In the case of generation of electricity, maintaining gas vapor at an appropriate pressure and flow rate to the steam generating furnace prevents undesirable disruption to the generator necessary for turbine operation. Such disruption can lead to shutting down the turbines until the problem is corrected.

To avoid such problems, vaporized gas conduit systems generally incorporate sensors and alarms which are triggered when sub-optimal conditions arise. Conventionally, upon detection of a gas flow/pressure anomaly, an alarm(s) will trigger in a control room to alert staff of the problem at which time a system operator will promptly access the gas line to verify the disruption and, if necessary, manipulate the appropriate valve either by adjusting or turning off the pipeline feed. As discussed, while systems can include a back-up vapor gas supply line to avoid the necessity of system shut down and a disruption of a feedstock injection into a pipeline or generation of electricity, an operator, after shutting down the first pipeline feed must access the second pipeline to open its valve(s) to maintain positive gas flow to the analyzers and/or to provide for flow to the furnace. However, the time required for the operator to access the first pipeline and, where the second pipeline is implicated, the second pipeline, may require several minutes and traversing distances required to move between remotely spaced facilities.

SUMMARY OF THE INVENTION

Illustrative, non-limiting embodiments of the present invention overcome the aforementioned and other disadvantages associated with related art gas sampling and conditioning systems. Also, the present invention is not required to overcome the disadvantages described above and an illustrative non-limiting embodiment of the present invention may not overcome any of the problems described above.

It is an object of the present invention to provide a novel gas sampling and conditioning system, as well as a method thereof, that overcomes problems associated with conventional sampling and conditioning systems.

It is an object of the present invention to provide a novel gas sampling and conditioning system that can maintain incoming gas pressures in the event of interruptions upstream of a gas sample input line or elsewhere in the system.

Objects of the invention are satisfied by a structure and method for providing multiple gas inputs from the source. Further objects of the invention are satisfied by providing a system capable of monitoring the pipeline gas flow and pressure of both primary and back-up pipelines and providing automatic switching therebetween. Such a system reduces nuisances caused by active alarms and the labor associated with scrambling to rectify the problematic gas line feed.

Still further objects of the invention are satisfied by providing a structure and method for automatically adjusting the gas sample input line based on pressure readings.

Further objects of the invention are satisfied by an automated multi-source switching adjunct and method for maintaining adequate pressure and flow rate of gas in a pipeline to maintain sample flow to a gas analyzer.

Other objects of the invention are satisfied by a structure and method that provide for purging gas line tubing of air to enhance gas line sample insertion efficiencies.

The present invention also satisfies additional objects by providing structures and methods for maintaining adequate gas flow for analysis with reduced risk of operational disruptions in case of sub-optimal flow conditions (i.e. rate and pressure).

To achieve these and other objects an embodiment in accordance with the invention includes a system for maintaining the pressure of a sample of natural gas from one or more gas transmission lines before directing the gas for conditioning and into a chromatograph or other analyzer.

As used herein "gas" means any type of gaseous matter capable of pipe transmission, including natural gas, biogas, organic gases, monomolecular gases, gas mixtures, and equivalents.

As used herein "connected" includes physical, whether direct or indirect, permanently affixed or adjustably mounted. Thus, unless specified, "connected" is intended to embrace any operationally functional connection.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings which are provided for illustration purposes as representative of specific exemplary embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

Given the following detailed description, it should become apparent to the person having ordinary skill in the art that the invention herein provides a novel gas maintenance system and a method thereof for providing significantly augmented efficiencies while mitigating problems of the prior art.

In accordance with one exemplary embodiment, a gas sampling and conditioning system is provided that includes a first probe device configured to extract a first gas sample from a gas source to a first gas sample input line and a second probe device configured to extract a second gas sample from the gas source to a second gas sample input line. Also included is an enclosure connected to the first and second gas sample input lines and configured to receive the first and second gas samples, the enclosure including a pressure switch configured to generate data representative of a pressure of the first gas sample, a microcontroller in communication with the pressure switch and configured to control flow of the first and second gas samples from the first and second gas sample input lines based on the data from the pressure switch, and gas conditioning equipment configured to receive and condition the first or second gas sample from the respective gas sample input line based on flow control by the microcontroller. The system further includes an analyzer device configured to receive the conditioned first or second gas sample from said gas conditioning equipment and determine constituent components therein.

In accordance with one exemplary embodiment, a multi-input auto-switching gas sampling and conditioning device is provided that includes an enclosure connected to first and second gas sample input lines and configured to receive corresponding first and second gas samples from the respective gas sample input lines, the enclosure including a pressure switch configured to generate data representative of a pressure of the first gas sample, a microcontroller in communication with the pressure switch and configured to control flow of the first and second gas samples from the first and second gas sample input lines based on the data from the pressure switch, and gas conditioning equipment configured to receive and condition the first or second gas sample from the respective gas sample input line based on flow control by the microcontroller and transfer the conditioned first or second gas sample to an analyzer device.

In accordance with one exemplary embodiment, a method of sampling and conditioning a gas sample is provided that includes the steps of: extracting a gas sample from a volume of gas to be conditioned, detecting a pressure of the gas sample and controlling the flow of the gas sample based on the pressure, heating the gas sample to a value within a predetermined temperature range, regulating the pressure of the vapor phase gas of the gas sample to a value within a predetermined pressure range, and outputting conditioned vapor phase gas within the predetermined temperature and pressure ranges to an analyzer for determination of the constituent components of the conditioned vapor phase gas.

BRIEF DESCRIPTION OF THE DRAWINGS

The aspects of the present invention will become more readily apparent by describing in detail illustrative, non-limiting embodiments thereof with reference to the accompanying drawings, in which:

FIG. 1 is diagrammatical partial cut-away front view of the interior of the multi-input auto-switching gas sampling and conditioning system connected to a remotely mounted enclosed gas probe on a pipeline according to one exemplary embodiment of the invention.

DETAILED DESCRIPTION OF ILLUSTRATIVE, NON-LIMITING EMBODIMENTS

Exemplary, non-limiting, embodiments of the present invention are discussed in detail below. While specific configurations and dimensions are discussed to provide a clear understanding, it should be understood that the disclosed dimensions and configurations are provided for illustration purposes only. A person skilled in the relevant art will recognize that other dimensions and configurations may be used without departing from the spirit and scope of the invention.

FIG. 1 illustrates a system 1 in accordance with the present invention. As shown, the system 1 of FIG. 1 comprises an enclosure, such as a cabinet 2 having, for example, a generally rectangular configuration. The cabinet shown in this embodiment can be composed of polymeric resin, stainless steel, or any other appropriate material or combination of materials, e.g., aluminum panels etc., that provide a substantially strong housing. Further, a cabinet suitable for housing a system in accordance with the present invention is sufficiently commodious to allow for a thick insulative lining. For example, to provide sufficient insulation, the insulating lining is approximately 1 inch thick or greater. Cabinet 2 also includes microcontroller 38 and corresponding electrical connections 39 for receiving and distributing electrical power in the system 1. The microcontroller 38 can further control the operation of solenoid valves 36, 37 via correspondingly connecting electrical connections 39. The cabinet 2 further includes gas conditioning equipment such as a vaporizing heated pressure regulator 42 and liquid block 44. The heated pressure regulator 42 is configured to maintain a desired constant gas pressure and temperature of a gas sample and the liquid block 44 is configured to separate any liquid from the gas sample. A corresponding relief/drain valve 46 is included to provide an output for expelling any heated gases, particularly contaminated heated gases, from the heated pressure regulator 42 and/or liquid from the liquid block 44. In accordance with an exemplary implementation, the liquid block 44 can be a membrane-type device that separates the liquid phase gases from vapor phase gases and provides the liquid phase portion for further processing. The cabinet 2 also includes and an indicator mechanism (not illustrated), such as a series of lights, wired to various connections within the junction box for indicating a status of current operations.

The exemplary cabinet 2 illustrated in FIG. 1 further includes an inlet/outlet port (not shown) for accommodating a power line to conduct electrical power, e.g., 110 volts A.C., 220 volts A.C., 12 volts D.C., 24 volts D.C., or any other suitable voltage required by components in or around cabinet 1 and specifically to electrical connections 39 and microcontroller 38.

Heated pressure regulator 42 can be, for example, a vaporizing pressure regulator that heats the gas both at its input and at its output. This is done to avoid adverse Joule-Thomson effects which can result in all or part of the gas changing phase into a wet gas or liquid as the gas pressure is changed, e.g., lowered to a pressure desirable by an analyzer device 47 (i.e. gas chromatograph). Accordingly, the heated pressure regulator 42 heats the gas before the pressure is changed and again after the pressure has been reduced to maintain the gas in the gas phase. In this manner, the potential for liquid creation due to hydrocarbon dew point dropout is greatly reduced. Heated pressure regulator 42 requires electrical power to generate and control its heat and, thus, is electrically connected to the electrical connections 39.

Gas pipes 50, such as ⅛ inch diameter stainless steel tubing, inside cabinet 2 can be for carrying gas samples from input ports 20, 22 and throughout the cabinet 2. Flow rate metering valves 32, 34 are provided in the flow path of the gas along gas pipes 50 and can be configured to control the flow rate of the gas based on specifications specific to the application of the system 1 when implementing a speed loop with outlet ports 28, 30, as described in U.S. Pat. Nos. 8,056,399, 9,285,299 and 9,562,833, the entirety of each of which is herein incorporated by reference. The flow rate metering valves 32, 34 can be adjusted based on readings from corresponding rotometers 26, 27. This can be done manually via manual inspection of the rotometers 26, 27 and/or automatically by microcontroller 38 based on signals from rotometers 26, 27.

Exemplary operation of the system 1 described above will now be provided in reference to FIG. 1. Further, additional reference as to aspects of the operation of the system 1 is described in U.S. Pat. No. 7,162,933, assigned to assignee of the present invention, Mustang Sampling, LLC of Ravenswood, W. Va., the entirety of which is herein incorporated by reference.

Gas, for example natural gas, being transported or otherwise stored within a device, e.g., pipe, 10, is sampled by sample probe devices 13, 15. For example, sample probes 13, 15 can be membrane-type gas probes that permit vapor phase gas to permeate through the membrane while preventing any liquid phase gases from passing through the probe. Once the sample having substantially all vapor phase gas is collected, the sample is directly input to optional intermediate enclosure devices 12, 14 where the sample is heated. For example, the intermediate enclosure device can be a Pony® device manufactured by Mustang Sampling, LLC. It should be noted that the intermediate enclosure device is optional and according to alternative embodiments of the present invention the intermediate enclosure device is eliminated.

A heated sample is output from the intermediate enclosure device and transported via sample gas input lines 16, 18 to respective input ports 20, 22 of cabinet 2. Sample gas input lines 16, 18 can include a stainless-steel tube through which the sample gas is transported and a heat tracing cable in close proximity to the stainless tube for heating the tube and, thus, the gas within the tube. Around the stainless tube and the heat tracing cable an insulating material and a shielding material, e.g., rubber, plastic, etc., can be provided.

Accordingly, as described herein, to avoid interruption or inconsistent pressure on a gas sample input line affecting the system, multiple gas sample input lines are provided in the system 1. Although only two gas sample input lines 16, 18 are shown, additional gas sample input lines could be implemented. In one exemplary implementation, however, at any given time, the system 1 will be in operation with only one of the gas sample input lines 16, 18, being used for analysis while the unused line(s) will direct samples out of the system via corresponding outlet ports (i.e. outlet port 28, 30) to be redirected back into the pipeline 10. For example, valves (i.e. solenoid valves) 36, 37 are provided downstream of gas inputs 20, 22 to control the flow of gas in the cabinet 2. In one example, both solenoid valves 36, 37 can be set to direct the flow of the gas sample to corresponding outlet ports, 28, 30, respectively. This setting can be maintained until a predetermined pressure is detected at juncture 52 by a pressure switch 24 at which point the pressure switch 24, or alternatively, the microcontroller 38, based on signals from pressure switch 24, can control solenoid valve 36 to control the flow towards outlet port 28. Alternatively, in one example, the cabinet can be pre-configured to have solenoid valve 36 control the flow towards outlet port 28 and solenoid valve 37 control the flow toward outlet port 30 immediately upon sampling.

In this configuration, input gas samples are directed past pressure switch 24 and through solenoid valve 36 to an adjustable metering valve 40 which controls the flow rate of gas. This control can be performed manually or automatically by microcontroller 38 based on signals at least from pressure switch 24 to ensure an acceptable flow rate to liquid block 44. The gas is then passed to the liquid block 44, where any liquid phase gas that is present is separated from the vapor phase gas and is transported via stainless tubing to relief drain 46 for further processing and/or storage. The vapor phase gas is output from liquid block 44 and is provided to heated vaporizing pressure regulator 42. Heated vaporizing pressure regulator 42 heats the inputted gas to within a certain temperature range, e.g., a temperature range determined by the hydrocarbon dew point curve of the particular gas sample, and reduces the pressure of the gas to a level that can be accommodated by the analyzer 47. For example, in the case of natural gas, the inputted pressure could be approximately 2000 psig and the pressure regulator would reduce this pressure to about 10-20 psig, e.g., a desirable pressure range for inputting gas to the analyzer 47 connected to cabinet 2 via outlet 48. Due to the significant pressure reduction in the gas, if the temperature of the gas were kept constant, the joule-Thomson effect dictates that hydrocarbon dew point dropout would occur and at least a portion, if not all, of the sample gas would change into its liquid phase. Accordingly, heated pressure regulator 42 is controlled by microcontroller 38 to heat the reduced-pressure gas to avoid the Joule-Thomson effect and maintain the sample gas in its vapor phase.

Pressure relief port 43 is optionally for relieving pressure in the event the pressure at the output of heated pressure regulator 42 is above the desired range. For example, if the desired range for the output of heated pressure regulator 42 is 10-20 psig and the output of heated pressure regulator 42 is 100 psig as detected by an internal sensor, pressure relief port 43 can open to permit sample vapor gas to escape outside cabinet 2 via port 46.

Having described the functionality and processing provided by the system 1 using pre-configured gas sample input line 18, an example will now be provided with respect to use of gas sample input line 16 due to a failure event(s) with respect to gas sample input line 18. Failures can take the form of blockage in the gas sample input line 18, issues retrieving the gas sample from pipeline 10, the malfunction of equipment such as the probes 13,15, and/or reduced pressure below an acceptable threshold for sampling and conditioning. In this example, it is assumed that the flow of gas from gas sample input line 18 gets reduced in pressure below an acceptable level for analysis. The drop in pressure on gas sample input line 18 will be detected at junction 52 by the pressure switch 24. The pressure switch 24 can be configured to any pressure threshold (i.e. 100 psi in this example) such that any sample detected at the junction 52 having a pressure less than 100 psi (i.e. interruption or pressure fluctuations) will result in pressure switch 24 sending a signal to microcontroller 38 which will control solenoid valve 36 to shunt the flow away from the metering valve 40 and toward the speed loop outlet port 28. At the same time as the microcontroller receives the signal from pressure switch 24, or shortly thereafter, the microcontroller 38 controls solenoid valve 37 to shunt the flow away from outlet port 30 and toward metering valve 40 for conditioning and sample analysis. In other words, the system 1 will no longer intake gas samples from input port 22 having upstream pressure issues and will instead intake samples from input port 20. This could continue indefinitely or, in one example, pressure switch 24 can revert the intake of gas samples back to input port 22 when detecting pressures above the predetermined pressure threshold (i.e. 100 psi) thereby indicating that there are no longer any upstream issues with respect to gas sample input line 18.

Pressure switch 24 is connected to electronic connections and microcontroller 38 thereby providing the ability of the pressure switch 24 and/or microcontroller 38 to provide control signals to de-energize or energize solenoid valves 36, 37 based on pressure readings. One example of a pressure switch is a PSW-400 series (i.e. PSW-408) switch manufactured by Omega Engineering, Inc. Such a switch can provide control based on pressures ranging at least from 40 psi to 200 psi. However, other pressure switches could be used to provide additional pressure range control functionality.

Accordingly, the multi-input auto switching functionality described herein provides the advantageous features of automatically switching gas sample input lines when there is an interruption or fluctuation in gas pressure coming from the pipeline 10 or other failure event upstream of input port 22. This immediately prevents issues arising out of non-constituent samples being provided to the analyzer 47, such as a gas chromatograph, leading to inaccurate readings as well as potential shutdowns or damage to the gas chromatograph. This in turn prevents downtime of the system 1 as reactivation of the gas chromatograph is time consuming and can be very costly. The ability to automatically control gas sample input lines also reduces labor costs and time as manual shutdown of one gas sample input line and activation of another distantly located gas sample input line is no longer required thereby reducing timeframes involving analysis of inaccurate non-constituent gas samples. Further, for industrial applications, the system is able to maintain gas vapor at appropriate pressure and flow rate to, for example, steam generating furnaces thereby preventing undesirable disruption to the generator necessary for turbine operation. This would also reduce nuisances caused by system alarms and associated labor.

Additional implementations and corresponding advantages are contemplated herein. For example, signals from faulty instrumentation downstream of pressure switch 24 could result in flow changes. Thus, in one example, microcontroller 38 could control valve 36 to deactivate input from input port 22 when it receives signals indicative of a faulty valve 36. Conversely, microcontroller 38 could control valve 37 to deactivate input from input port 20 when it receives signals indicative of a faulty valve 37. Additional sensors, such as pressure sensors, could be located along the flow of the gas sample from juncture 52 to outlet port 28, or similarly, input port 20 to outlet port 30, which could provide signals to microcontroller 38 indicative of failure events along those flow paths thereby resulting in microcontroller 38 controlling valve 36 or 37, accordingly. Further, if a failure event is detected at any point in the flow of a gas sample from the pipeline 10 to flow meter 40, such as failure events on flow paths from both sample input line 16 and sample input line 18, the microcontroller 38 could control respective controlling valve 36 or 37, accordingly, and/or cause flow meter 40 to completely restrict the flow of the gas sample to prevent possible damage to downstream conditioning equipment such as the heated pressure regulator 42 and liquid block 44.

Although several embodiments of the invention have been disclosed in the forgoing specification, it is understood by those skilled in the art that many other modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

While various aspects of the present invention have been particularly shown and described with reference to the exemplary, non-limiting, embodiments above, it will be understood by those skilled in the art that various additional aspects and embodiments may be contemplated without departing from the spirit and scope of the present invention.

It would be understood that a device or method incorporating any of the additional or alternative details mentioned above would fall within the scope of the present invention as determined based upon the claims below and any equivalents thereof.

Other aspects, objects and advantages of the present invention can be obtained from a study of the drawings, the disclosure and the appended claims.

What is claimed is:

1. A multi-input auto-switching gas sampling and conditioning system for hydrocarbon containing natural gas, comprising:
    a first probe device configured to extract a first gas sample at a first pressure from a gas source to a first gas sample input line;
    a second probe device configured to extract a second gas sample from the gas source to a second gas sample input line;
    an enclosure connected to the first and second gas sample input lines and configured to receive the first and second gas samples, the enclosure including;
    a pressure switch configured to detect the first pressure and generate data representative of said first pressure of the first gas sample;
    a flow rate metering assembly connected to said first gas input line;
    a first outlet port for redirecting flow of the first gas sample from said first gas sample input line;
    a second outlet port for redirecting flow of the second gas sample from said second gas sample input line;
    a microcontroller in communication with the flow rate metering assembly and pressure switch and configured to control flow of the first and second gas samples from the first and second gas sample input lines based on the data from the pressure switch wherein the microcontroller discontinues the flow of the first gas sample as a function of data from the pressure switch indicative of the first pressure being less than a predetermined threshold or the flow rate being below an acceptable minimum to prevent hydrocarbon dew point dropout and to direct the first gas sample to said first outlet port while automatically redirecting the second gas sample flow from the second outlet port, and
    gas conditioning equipment configured to receive and condition the first or second gas sample from the respective gas sample input line based on flow control by the microcontroller wherein said gas conditioning equipment includes a pressure regulator configured to heat and regulate the pressure of the first or second gas sample; and
    an analyzer device configured to receive the conditioned first or second gas sample from said gas conditioning equipment and determine constituent components therein.

2. The system as recited in claim 1, wherein said pressure regulator heats the first or second gas sample and reduces the pressure of the first or second gas sample to maintain a sample compatible with the analyzer device.

3. The system as recited in claim 1, wherein said gas conditioning equipment includes:
    a liquid block configured to receive the first or second gas sample and separate liquid phase constituent components from vapor phase constituent components of the sample.

4. The system as recited in claim 3, wherein the microcontroller controls flow of the first and second gas sample by controlling first and second valves connected to the first gas sample input line and second gas sample input line, respectively.

5. The system as recited in claim 4, wherein, when the pressure switch detects that the pressure of the first gas sample is less than 100 psi, the microcontroller causes the first valve to direct flow to a bypass outlet and causes the second valve to direct flow of the second gas sample to the gas conditioning equipment.

6. A multi-input auto-switching hydrocarbon containing natural gas sampling and conditioning device comprising:
    an enclosure connected to first and second gas sample input lines and configured to receive corresponding first and second gas samples from the respective gas sample input lines, the enclosure including
    a pressure switch configured to generate data representative of a pressure of the first gas sample,
    a microcontroller in communication with the pressure switch and configured to control flow of the first and second gas samples from the first and second gas sample input lines based on the data from the pressure switch as a function of data from the pressure switch indicative of the pressure being below a predetermined threshold,
a first outlet connected with the first gas sample input line and a second outlet connected to the second gas input line where the microcontroller switches said first gas sample to the first gas outlet upon receiving data from the pressure switch indicative of pressure below the predetermined threshold; and
gas conditioning equipment including a pressure regulator configured to heat and regulate the pressure of the first or second gas sample configured to receive and condition the first or second gas sample from the respective gas sample input line to prevent hydrocarbon dew point dropout based on flow control by the microcontroller and transfer the conditioned first or second gas sample to a downstream device.

7. The device as recited in claim 6, wherein said pressure regulator heats the first or second gas sample and reduces the pressure of the first or second gas sample to maintain a sample compatible with the analyzer device.

8. The device as recited in claim 6, wherein said gas conditioning equipment includes:
a liquid block configured to receive the first or second gas sample and separate liquid phase constituent components from vapor phase constituent components of the sample.

9. The device as recited in claim 8 wherein the microcontroller controls flow of the first and second gas sample by controlling first and second valves connected to the first gas sample input line and second gas sample input line, respectively.

10. The device as recited in claim 9, where the microcontroller causes the first valve to direct flow to said first outlet and causes the second valve to direct flow of the second gas sample to the gas conditioning equipment.

11. A method of sampling and conditioning a hydrocarbon containing natural gas sample comprising:
providing a first gas sample take-off from a gas sample source;
providing a second separate sample take-off from a gas sample source;
extracting a gas sample from said first takeoff source to be conditioned;
detecting a pressure of the extracted gas sample to meet a predetermined minimum pressure threshold,
detecting the flow rate of the extracted gas sample to meet an acceptable minimum;
discontinuing the gas sample extraction from the first sample take-off upon detection of a pressure below the predetermined minimum pressure or a flow rate below the acceptable minimum and switching extraction to the second sample take-off to maintain the gas sample in its vapor phase;
heating the gas sample to a value within a predetermined temperature range;
regulating the pressure of the vapor phase gas of the gas sample to a value within a predetermined pressure range to prevent hydrocarbon dew point dropout; and
outputting conditioned vapor phase gas within the predetermined temperature and pressure ranges to an analyzer for determination of the constituent components of the conditioned vapor phase gas.

* * * * *